United States Patent [19]

Mathiaparanam

[11] Patent Number: 4,736,036

[45] Date of Patent: Apr. 5, 1988

[54] PROCESS FOR THE PREPARATION OF QUINOLINIC ACID

[75] Inventor: Ponnampalam Mathiaparanam, Appleton, Wis.

[73] Assignee: Appleton Papers Inc., Appleton, Wis.

[21] Appl. No.: 521,211

[22] Filed: Aug. 8, 1983

[51] Int. Cl.$^4$ ................................. C07D 213/807
[52] U.S. Cl. ........................................ 546/320
[58] Field of Search ................................. 546/320

[56] References Cited

FOREIGN PATENT DOCUMENTS 0034943 9/1981 European Pat. Off. .
0024197 2/1981 European Pat. Off. .

OTHER PUBLICATIONS

Ayres, D. C., et al., "Oxidation of Aromatic Substrates, Part II", J. Chem. Soc. Perkin I (1975), pp. 707-710.

Chemical Abstracts, vol. 83, No. 3, p. 485, Column 2, Abstract No. 27980V.

Chemical Abstracts, vol. 57, No. 12, Abstract No. 15080C.

Hoffman, P. N., "The Stability of Sodium Hypochlorite Solutions", Soc. Appl. Bacteriol. Tech. Ser. (1981) 16 (Disinfect.: Their use Eral. Eff.), pp. 77-83.

*Primary Examiner*—Henry R. Jiles
*Assistant Examiner*—Dale A. Bjorkman
*Attorney, Agent, or Firm*—E. Frank McKinney; Paul S. Phillips, Jr.

[57] ABSTRACT

A process is disclosed for the manufacture of quinolinic acid by oxidizing quinoline with ruthenium tetraoxide in the presence of hypochlorite solution in which a certain amount of base is added prior to the inception of the oxidation reaction. The disclosed process provides greatly improved yields of high purity quinolinic acid.

14 Claims, No Drawings

PROCESS FOR THE PREPARATION OF QUINOLINIC ACID

The present invention relates to a process for the manufacture of quinolinic acid.

Quinolinic acid is used as an intermediate for the synthesis of pharmaceuticals, insecticides, pigments and dyes. Of particular recent importance has been the use of quinolinic acid for the synthesis of chromogenic materials such as those disclosed in U.S. Pat. No. 3,775,424, which is hereby incorporated by reference. In such processes, quinolinic acid is converted to the anhydride such as by reaction with acetic anhydride at 130° C. for 10 minutes. The resulting 2,3-pyridine dicarboxylic anhydride can then be reacted with an indole to form ketones such as disclosed in Example VI of U.S. Pat. No. 3,775,424. These ketones can then be further reacted, such as, for example, with N,N-diethyl-m-phenetidine to produce useful chromogenic pyridinone compounds as disclosed in U.S. Pat. No. 4,246,318.

Quinolinic acid has heretofore been obtained by the oxidation of quinoline with hydrogen peroxide in the presence of copper sulfate as taught in U.S. Pat. No. 4,316,026. While this process represented a considerable advance in the art through the use of particular reaction conditions, the reaction itself is exothermic and in order to maintain control, must be performed at a lower than optimum temperature, lowering the rate of reaction, increasing reaction time and increasing the opportunity for the occurrence of side reactions.

A substantial improvement over the process of U.S. Pat. No. 4,316,026, described and claimed in U.S. patent application Ser. No. 236,945 of Seishi Ikegami et al. filed Feb. 20, 1981, resulted from the combination of reduced pressure and reuse of the reaction media. This latter process, nevertheless, requires the use of more complicated and expensive equipment and utilizes an oxidizing agent which can be decomposed, sometimes explosively, by the presence of certain contaminants such as rust.

D. C. Ayres and A. M. M. Hossain, *J. Chem. Soc. Perkin I*, 707 (1975), oxidized quinoline with ruthenium tetraoxide to form quinolinic acid which was isolated and characterized as the dimethyl ester. This particular reaction was very inefficient in the oxidation since 60% of the unreacted quinoline was recovered. Of the remaining 40% of the quinoline, 45% was recovered as the dimethyl ester of quinolinic acid. This represents an overall yield of only 18% based on total quinoline employed.

It has now been surprisingly found that when quinoline is oxidized with ruthenium tetraoxide in the presence of hypochlorite solution and base at or above a certain base:quinoline ratio, unexpectedly higher yields of higher purity quinolinc acid are produced over that resulting from the Ayres et al. disclosure.

It is, therefore, an object of the present invention to provide a process for producing quinolinic acid in high yield and high purity by oxidizing quinoline with ruthenium tetraoxide in the presence of hypochlorite solution wherein a suitable base is added in an amount sufficient to provide a base to quinoline ratio within a specified range.

The present invention provides a process for the preparation of quinolinic acid by oxidizing quinoline with ruthenium tetraoxide in the presence of hypochlorite solution in which a certain amount of base is added prior to the inception of the oxidation reaction. In this reaction, the primary oxidant is ruthenium tetraoxide which is produced from ruthenium trichloride by the secondary oxidant, the hypochlorite. In the process of oxidizing the quinoline, the ruthenium tetraoxide is reduced to ruthenium dioxide. The ruthenium dioxide, however, is, in turn, oxidized to ruthenium tetraoxide by the hypochlorite. The oxidation of quinoline when conducted in the presence of hypochlorite solution as a secondary oxidant, can therefore be performed with any one or any combination of the ruthenium compounds mentioned (namely, ruthenium trichloride, ruthenium tetraoxide or ruthenium dioxide) since the effective primary oxidant, ruthenium tetraoxide, will either be present or produced under the conditions employed.

Hypochlorite solution contains a certain amount of base as a consequence of the method used to manufacture the hypochlorite. This residual base tends to act as a stabilizer for the hypochlorite solution. Unexpectedly improved yields of quinolinic acid are obtained when the reaction media is supplemented with additional base in an amount sufficient to bring the total base to quinoline ratio to or above a certain specified amount.

The amount of base which must be added depends upon the strength of the base. For strong bases such as, for example, sodium hydroxide and potassium hydroxide, sufficient base needs to be added to the reaction media to bring the molar ratio of the total base to quinoline to about 5 or greater. The upper limit is decided more by economic considerations than any additional beneficial effect on the reaction. A molar ratio of base:quinoline as high as 24:1 when sodium hydroxide was employed as the base has been found to provide unexpectedly enhanced yields. For strong bases a base:quinoline molar ratio of about 7:1 to about 12:1 is more preferred.

For weaker bases such as, for example, sodium carbonate or potassium carbonate, the total base to quinoline molar ratio should be about 4:1 or greater.

The process of the present invention involves preparing a mixture of quinoline, ruthenium trichloride, and base. While this mixture is stirred vigorously, hypochlorite solution is added and the stirring is continued for the duration of the reaction. The quinolinic acid is normally recovered from the reaction media by precipitation as copper quinolinate. The copper quinolinate is converted to quinolinic acid in a nearly quantitative manner by dispersing the copper quinolinate in water, heating to about 60° C. and passing hydrogen sulfide gas through the dispersion.

When a weak base is used, the process of the present invention additonally requires the use of carbon tetrachloride. The process can optionally utilize carbon tetrachloride when a strong base is employed but its use is not required to derive the benefits of the present invention. The hypochlorite solution can be any common metallic salt of hypochlorous acid but sodium hypochlorite in the weight percent range of about 5 to 15% is most commonly used because it is readily available. Potassium hypochlorite is a suitable alternative. The theoretical amount of hypochlorite solution required for the oxidation is about 8 moles per mole of quinoline. Due to decomposition of the hypochlorite at elevated temperatures additional hypochlorite beyond the theoretical amount must be employed to compensate for the decomposition. This amount can be determined without undue experimentation.

Most water-soluble inorganic bases, either strong or weak, are suitable for the performance of this invention. Exemplary of strong water-soluble bases are sodium hydroxide and potassium hydroxide and of weak water-soluble bases are sodium carbonate and potassium carbonate.

The oxidation reaction is preferably performed at a temperature of from about 20° C. to about 60° C. More preferred is the temperature range of about 40° C. to about 55° C.

The process should be run for sufficient time to permit completion of the reaction. Twenty hours is usually sufficient but longer periods of time do not appear to adversely affect the yields.

The following examples are given merely as illustrative of the present invention and are not to be considered as limiting. All parts and percentages throughout the application are by weight, unless specified otherwise. All solutions, unless otherwise designated, are aqueous solutions.

EXAMPLES 1–13

This series of experiments was designed to determine the critical total base to quinoline molar ratio when a strong base is added to reaction media prior to the inception of the oxidation reaction. For each of these 13 experiments the following procedure was employed.

The following amounts, volumes and reaction conditions were utilized in each of the 13 experiments:

| | |
|---|---|
| amount of quinoline | 5.2 grams, 0.04 mole |
| amount of sodium hypochlorite | 0.44 mole |
| amount of ruthenium trichloride | 0.01 gram, 3.8 × 10$^{-5}$ mole |
| volume of carbon tetrachloride | 20 ml. |
| volume of aqueous phase | 350 ml. |
| reaction temperature | 50° C. |
| reaction time | 20 hours |

Prior to each experiment, the hypochlorite solution employed was analyzed for the amount of base present and the concentration of the hypochlorite. The amount of base found in the hypochlorite solutions employed typically contributed to the base to quinoline ratio in the range of from 0.625:1 to 1.5:1.

For each experiment, a mixture of 5.2 grams of quinoline, 0.01 gram of ruthenium trichloride trihydrate and sufficient sodium hydroxide to provide the desired total base to quinoline molar ratio was stirred vigorously and sufficient sodium hypochlorite solution to provide 0.44 mole of sodium hypochlorite was added to the stirring mixture. The sodium hydroxide was added in a volume of water determined by the difference between 350 ml. and the volume of sodium hypochlorite solution utilized. The stirring mixture was heated to 50° C. and the stirring and heating was maintained under reflux conditions for 20 hours.

The quinolinic acid product from each reaction was recovered from the cooled reaction mixture by the following procedure. The aqueous layer was separated from the reaction mixture, 10 ml. of isopropyl alcohol were added and the resulting liquid was filtered to remove insoluble material. The filtrate was acidified to pH 1.0 with dilute sulfuric acid, 20 grams of copper sulfate pentahydrate in 30 ml. water were added, the mixture was heated to 80° C. for 30 minutes and the precipitated copper quinolinate was removed by filtration and dried in an oven at 100° C. for 2 to 3 hours.

Using the above procedure Examples 1–13 were prepared. The molar ratio of total base (the amount found by analysis in the hypochlorite solution plus the amount added) to quinoline and the corresponding yield of copper quinolinate are entered in Table 1 for Examples 1–13.

TABLE 1

| Example | molar ratio of total base to quinoline | Yield of copper quinolinate (%) |
|---|---|---|
| 1 | 1 | 0 |
| 2 | 2 | trace |
| 3 | 3 | 21 |
| 4 | 4 | 46 |
| 5 | 5 | 74 |
| 6 | 6 | 76 |
| 7 | 7 | 83 |
| 8 | 8 | 81 |
| 9 | 9 | 92 |
| 10 | 10 | 82 |
| 11 | 12 | 92 |
| 12 | 14 | 75 |
| 13 | 24 | 73 |

EXAMPLES 14–22

Examples 14–22 were performed using the same procedure as was used for Examples 1–13 except that the added base was sodium carbonate rather than sodium hydroxide. Listed in Table 2 are the molar ratio of total base to quinoline and yield of copper quinolinate for each Example.

TABLE 2

| Example | molar ratio of total base to quinoline | Yield of copper quinolinate (%) |
|---|---|---|
| 14 | 2 | 35 |
| 15 | 3 | 43 |
| 16 | 4 | 51 |
| 17 | 5 | 51 |
| 18 | 6 | 54 |
| 19 | 7 | 59 |
| 20 | 8 | 54 |
| 21 | 9 | 54 |
| 22 | 10 | 60 |

EXAMPLE 23

A mixture of 5.2 grams of quinoline, 0.01 gram ruthenium trichloride trihydrate, 20 ml. of carbon tetrachloride and 12.3 grams of potassium hydroxide in 20 ml. of water was stirred vigorously and 260 ml. of 12.7% sodium hypochlorite solution was added to the stirring mixture. The stirring mixture was heated to 50° C. and refluxed at 50° C. with stirring for 20 hours. The quinolinic acid product from the above reaction was recovered from the reaction mixture by the same procedure as in Examples 1–13. The yield of quinolinic acid in the form of copper quinolinate was 7.8 grams (74%).

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for the preparation of quinolinic acid by oxidizing quinoline with ruthenium tetraoxide in the presence of hypochlorite solution and a base selected from the group consisting of sodium hydroxide and potassium hydroxide, wherein the molar ratio of total base to quinoline is at least 5:1.

2. The process of claim 1 wherein the hypochlorite solution is selected from the group consisting of sodium hypochlorite and potassium hypochlorite.

3. The process of claim 2 wherein the hypochlorite solution is sodium hypochlorite.

4. The process of claim 3 wherein the base is sodium hydroxide.

5. The process of claim 4 which additionally comprises carbon tetrachloride.

6. The process of claim 5 wherein the molar ratio of base to quinoline is from about 7:1 to about 12:1.

7. The process of claim 3, 4 or 5 wherein the oxidation is conducted at a temperature of about 20° C. to about 60° C.

8. The process of claim 7 wherein the oxidation is conducted at a temperature of about 40° C. to about 55° C.

9. A process for the preparation of quinolinic acid by oxidizing quinoline with ruthenium tetraoxide in the presence of hypochlorite solution, carbon tetrachloride and a base selected from the group consisting of sodium carbonate and potassium carbonate, wherein the molar ratio of total base to quinoline is at least 4:1.

10. The process of claim 9 wherein the hypochlorite solution is selected from the group consisting of sodium hypochlorite and potassium hypochlorite.

11. The process of claim 10 wherein the hypochlorite solution is sodium hypochlorite.

12. The process of claim 11 wherein the base is sodium carbonate.

13. The process of claim 10, 11 or 12 wherein the oxidation is conducted at a temperature of about 20° C. to about 60° C.

14. The process of claim 13 wherein the oxidation is conducted at a temperature of about 40° C. to about 55° C.

* * * * *